United States Patent [19]

Chasin et al.

[11] 4,313,847
[45] Feb. 2, 1982

[54] SURFACTANT COMPOSITIONS

[75] Inventors: David G. Chasin; Thomas J. Zaucha, both of Wilmington, Del.

[73] Assignee: ICI Americas Inc., Wilmington, Del.

[21] Appl. No.: 42,626

[22] Filed: May 25, 1979

Related U.S. Application Data

[63] Continuation-in-part of Ser. No. 915,700, Jun. 15, 1978, abandoned.

[51] Int. Cl.$^3$ .................. B01F 17/14; B01F 17/16; B01F 17/34; B01F 17/42
[52] U.S. Cl. .................. 252/356; 71/64 R; 71/65; 71/94; 71/100; 71/118; 71/121; 252/357; 252/DIG. 17; 424/170
[58] Field of Search ............ 252/356, 357, 174.16, 252/DIG. 17

[56] References Cited

U.S. PATENT DOCUMENTS

| | | | |
|---|---|---|---|
| 2,845,380 | 7/1958 | Mayhew et al. | 71/DIG. 1 |
| 3,004,056 | 10/1961 | Nunn, Jr. et al. | 252/DIG. 1 |
| 3,307,931 | 3/1967 | Unger et al. | 71/2.2 |
| 3,314,891 | 4/1967 | Schmolka et al. | 252/174.16 X |
| 3,317,305 | 5/1967 | Stefcik et al. | 71/3 |
| 3,741,912 | 6/1973 | Kaneko | 252/529 |
| 3,741,913 | 6/1973 | Waag | 252/174.16 X |
| 3,869,399 | 3/1975 | Collins | 252/DIG. 1 |
| 3,948,636 | 4/1976 | Marks | 71/DIG. 1 |
| 3,970,595 | 7/1976 | Ginn et al. | 252/DIG. 1 |
| 4,070,298 | 1/1978 | Scardera et al. | 252/DIG. 1 |
| 4,070,309 | 1/1978 | Jacobsen | 252/544 |
| 4,105,592 | 8/1978 | Collins | 252/DIG. 1 |

FOREIGN PATENT DOCUMENTS 2389671 12/1978 France .................. 252/135

OTHER PUBLICATIONS

McCutcheon, Detergents & Emulsifiers (1975 Ann.), MC Pub. Co, Ridgewood, N.J., pp. 65, 66, 68, 69, 78, 160, 161 (1975).
McCutcheon, Detergents & Emulsifiers (1970 Ann.), Allured Pub. Co., Ridgewood, N.J., pp. 80, 220, 221, 252 (1970).
Griffin, "Calculation of HLB Values of Non-Ionic Surfactants", The American Perfumer & Essential Oil Review, May 1955, pp. 26-29.
McCutcheon's Detergents & Emulsifiers, No. American Edition, 1973 Annual, Publ. by McCutcheon's Div., Allured Publ. Corp., p. 174.

*Primary Examiner*—Richard D. Lovering

[57] ABSTRACT

Surfactant compositions, which are particularly useful in the preparation of concentrated pesticide-containing formulations, are disclosed. The surfactant compositions contain (a) a polyoxyalkylene alkyl or alkylaryl ether phosphate ester, (b) a polyoxyalkylene alkyl amine, and (c) a material selected from the group consisting of nonionic polyoxyalkylated surfactants, polyhydric alcohol esters and polyoxyalkylene glycols.

4 Claims, No Drawings

SURFACTANT COMPOSITIONS

This application is a continuation-in-part of copending application Ser. No. 915,700, filed June 15, 1978 now abandoned.

BACKGROUND OF THE INVENTION

1. Field of the Invention

The present invention relates generally to a surfactant composition; to a concentrated pesticide-containing formulation prepared from said surfactant composition; and to a pesticide suspension or emulsion suitable for use in agriculture and related areas. More particularly, the invention relates to a surfactant composition comprising (a) a polyoxyalkylene alkyl or alkylaryl ether phosphate ester, such as a polyoxyethylene nonyl phenol phosphate ester, (b) a nonionic polyoxyalkylene alkyl amine, and (c) a material selected from the group consisting of nonionic polyoxyalkylated surfactants; polyhydric alcohol esters and polyoxyalkylene glycols; to a concentrated formulation comprising said surfactant composition, a pesticide and a suitable vehicle or diluent; and to an emulsion or suspension comprising a dispersion of said concentrated formulation in an aqueous medium.

2. Description of the Prior Art

Numerous synthetic, organic, biologically active materials are now commercially available and are useful for a wide variety of applications. These materials include insecticides, insect repellents, herbicides, fungicides, acaricides, nematocides, molluscicides, rodenticides, and the like. All of these materials are referred to herein by the generic term pesticides. In use, it is generally desirable to spray these materials onto a substrate (plant, animal, etc.) or area to be treated. Because of its availability, minimal cost, and lack of adverse environmental effects, it is preferred to apply these materials from an aqueous medium. However, many of these materials are insoluble in water and can be dissolved only in organic solvents. For this reason, such pesticides are conventionally, admixed with emulsifying agents and organic solvents to form concentrates which are subsequently added to water in small quantities to form emulsions. These concentrates are referred to herein as "emulsifiable concentrates". Other of these pesticides are not soluble either in water or in organic solvents. Concentrated formulations of these pesticides are generally prepared either as "wettable powders" or as "flowable formulations". In preparing a wettable powder from solid pesticide, the pesticide is finely ground and combined with an inert solid diluent such as kaolin, attapulgite clays, diatomaceous earth, etc., and a surfactant. When added to water in the desired quantity the wettable powder forms a stable suspension in the water. Wettable powders may also be prepared from a liquid pesticide by combining the liquid pesticide with a finely ground adsorbent carrier such as diatomaceous earth or a hydrated calcium silicate. Surfactants are added to these liquid pesticide/carrier blends so that the wettable powder will form a stable suspension when added to water. A flowable formulation is commonly a concentrated dispersion of a finely ground pesticide in a liquid medium. However, flowables can also be concentrated dispersions of liquid pesticides in a suitable dispersion medium. The dispersion medium used in these flowable formulations may be water, which is most commonly used, or an organic liquid, such as a low viscosity, paraffinic oil. The flowable formulations are stabilized by the addition of surfactants and thickening agents. Other ingredients which are conventionally employed in concentrated, pesticide-containing formulations include, for example, antifoam agents and freezing point depressants in flowable formulations and anti-caking agents in wettable powders. Another type of concentrated, pesticide-containing formulation is a flowable emulsion. This is a concentrated, stable emulsion prepared from an emulsifiable concentrate and water. Additives and surfactants such as those discussed above in connection with flowable formulations may be used in these emulsions. When added to water all of the flowable formulations form a stable suspension of the pesticide in the water. In addition to making it possible to apply the pesticides in an aqueous medium, use of these concentrated formulations also makes it easier to handle and market the pesticides.

Numerous types of emulsifying agents, surface active agents (surfactants), and combinations and blends of said agents have been suggested for use in preparing concentrated formulations of pesticides. However, the manner in which it is desired to use the pesticides in both farm and household applications places severe demands upon the emulsifiers and surfactants which are used in the preparation of these formulations. When an emulsifiable concentrate containing a pesticide, usually dissolved in a suitable organic solvent, and an emulsifier is added to water in the desired proportions, it is important that there be a rapid, in fact almost spontaneous, dispersion of the pesticide so that relatively little, if any, stirring or agitation is required. Furthermore, since the water to which the concentrate is added may vary widely in hardness, depending upon local conditions, it is necessary that the emulsifier be such that the desired rapid dispersion is affected, in the available water of given hardness. Also, particularly in recent years, it has become common practice to apply a combination of pesticides simultaneously meaning that a given emulsifier system must be useful with a variety of pesticides or at least be compatible with the other pesticide formulations with which it is to be combined. Finally, it is also becoming common practice to apply pesticides in combination with a liquid fertilizer—i.e., an aqueous solution of inorganic plant nutrients formulated to provide specific amounts of nitrogen, phosphorus and potash together with minor amounts of other trace elements. This is generally done by adding an emulsifiable concentrate of the pesticide to an aqueous based liquid fertilizer and preparing an emulsion of said pesticide directly in said liquid fertilizer instead of in standard water. In this application, the emulsifier used must be compatible with the liquid fertilizer and capable of forming a stable emulsion therewith.

Currently, when an emulsifiable concentrate designed for use in water is used in a liquid fertilizer, it is frequently necessary to use a compatibility agent to obtain a satisfactory dispersion. This is generally a surfactant which is added to the tank mix of liquid fertilizer prior to adding the emulsifiable concentrate. A compatibility agent may also be required when a concentrate designed for use in liquid fertilizers is used in water or when a combination of pesticide formulations is to be utilized. Although compatibility agents are useful, they are not preferred since their addition is not within the control of the manufacturer of the concentrated pesticide formulation, they must be carefully selected so as not to adversely affect the pesticide employed, and their use introduces a number of human and mechanical variables (addition, mixing, etc.) all of which can adversely affect pesticide performance if not carefully controlled.

The same requirements and problems discussed above in connection with emulsifiable concentrates also apply with respect to wettable powders and flowable formulations. It would, therefore, be desirable to have an emulsifier/surfactant composition that could be used in the preparation of concentrated, pesticide-containing formulations (emulsifiable concentrates, wettable powders, flowable formulations and flowable emulsions) which could be used to form stable emulsions or suspensions in a variety of naturally occurring waters, as well as in liquid fertilizers and in combination with other pesticide formulations without the need for an additional compatibility agent.

SUMMARY OF THE INVENTION

In accordance with the present invention, an improved emulsifier/surfactant composition which is useful in the preparation of concentrated pesticide-containing formulations which are compatible with a wide variety of other pesticide-containing materials and which will form stable emulsions or suspensions in a wide range of naturally occurring waters as well as in liquid fertilizers has been discovered. This composition comprises (a) a polyoxyalkylene alkyl or alkylaryl ether phosphate ester, (b) a polyoxyalkylene alkyl amine, and (c) a material selected from the group consisting of nonionic polyoxyalkylated surfactants, polyhydric alcohol esters and polyoxyalkylene glycols.

DESCRIPTION OF THE PREFERRED EMBODIMENTS

As noted above, the surfactant compositions of the present invention contain three essential components giving these compositions a unique combination of properties not found in the previously available surfactants or combinations of surfactants. Each of these components is discussed separately below. It should be noted that each of these materials may be a polyoxyalkylene derivative of a given material. Such materials have previously been referred to as "alkylene oxide adducts" or, specifically, as "ethylene oxide, propylene oxide, etc. adducts". In general, these products are mixtures of compounds containing different numbers of alkylene oxide groups or mols of alkylene oxide, of which one predominates, being accompanied by smaller proportions of compounds containing larger and smaller numbers of the alkylene oxide groups in the polyoxyalkylene portion of the molecule. The products are identified by the number of mols of alkylene oxide reacted with each mol of the identified material. Thus, the term "polyoxyethylene(40)castor oil" refers to a material prepared by reacting 40 mols of ethylene oxide with 1 mol of castor oil.

(a) Polyoxyalkylene alkyl or alkylaryl ether phosphate ester

The first essential component of the surfactant compositions of the present invention is a phosphate ester of a polyoxyalkylene alkyl or alkylaryl ether.

These materials may be represented by the following general formula:

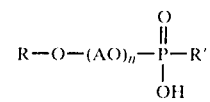

Wherein

R is a higher alkyl or alkylaryl radical wherein the alkyl portion contains at least about 4 carbon atoms, n is a positive integer equal to the number of mols of alkylene oxide used in the preparation of these materials, and is preferably equal to from about 4 to about 14, each A is an alkylene group, usually ethylene and/or propylene, and R' is hydroxyl or the radical R—O—(AO)$_n$ wherein R, A and n are as indicated above.

If R' is hydroxyl the material is a monoester. If R' is R—O—(AO)$_n$ the material is a diester.

These materials are generally prepared in two stages. In the first an alkyl alcohol or an alkylphenol is reacted with an alkylene oxide or a mixture of alkylene oxides. The resulting product is then converted to the phosphate ester. Procedures for carrying out these reactions are well known to those skilled in the art.

The preferred phosphate esters used in the present invention are derived from alkyl phenols such as octyl phenol, nonyl phenol and dinonyl phenols. Especially preferred phosphate esters are the polyoxyethylene nonyl phenol phosphate esters. These materials may be prepared by reacting nonyl phenol with ethylene oxide to prepare a polyoxyethylene nonyl phenol and reacting the resulting product with a phosphorylating agent, such as phosphoric anhydride ($P_2O_5$), to prepare the phosphate ester.

The nonyl phenol may be either para-nonyl phenol or a mixture of ortho-nonyl phenol and para-nonyl phenol. The nonyl phenol is reacted with ethylene oxide by procedures which are well known to those skilled in the art to prepare a polyoxyethylene nonyl phenol. The amount of ethylene oxide employed is generally equal to from about 4 to about 14 mols per mol of nonyl phenol. Particularly satisfactory results have been achieved with a material containing 8 mols of ethylene oxide and identified as polyoxyethylene(8)nonyl phenol. The ethylene oxide adduct of nonyl phenol is preferably reacted with phosphoric anhydride in a ratio of 3 mols of polyoxyethylene nonyl phenol to 1 mol of phosphoric anhydride to prepare a product which is a mixture of the monoester and the diester. As the ratio of nonyl phenol derivative to $P_2O_5$ is reduced toward 1 to 1 the amount of monoester in the mixture increases. In carrying out this reaction, the $P_2O_5$ is added over a period of time to the polyoxyethylene nonyl phenol. The reaction is exothermic and, if desired, can be cooled to prevent the temperature from going so high as to produce discolored and darkened products. The reaction proceeds continuously during the addition of the $P_2O_5$ and may be completed by allowing the mixture to stir until all of the $P_2O_5$ has dissolved. The resulting material may also contain some unreacted polyoxyethylene nonyl phenol. This may function as part of component (c) of the composition of the present invention.

The amount of phosphate ester used in the surfactant compositions of the present invention can be varied over a wide range depending upon the other materials used in said composition, the pesticide with which the composition is to be utilized, the organic solvents used to dissolve the pesticide or other formulation ingredients, and the nature of the aqueous medium (soft water, hard water, liquid fertilizer, mixture of pesticides, etc.) with which it is to be utilized. Generally, amounts of this component equal to from about 20% to about 80% have produced satisfactory results.

For a general purpose surfactant composition useful in a wide variety of applications, it has been found that amounts of polyoxyethylene nonyl phenol phosphate ester equal to from about 20% to about 80% by weight based upon the total weight of the surfactant composition are preferred. As mentioned below, especially preferred results have been achieved with compositions containing 42% and 67% by weight of a polyoxyethylene nonyl phenol phosphate ester. Although, as indicated above, there are a number of variables which determine the exact amount of this component to be utilized, it has generally been found that this component affects the usefulness of the composition in preparing emulsifiable concentrates and other formulations that will be utilized in hard water and that if it is left out performance in liquid fertilizers and hard water is adversely affected. Similarly, if too little of this component is included in the composition, performance in these media will be adversely affected. Of course, if the emulsifier composition is to be utilized in a material which will not be used in this media, lesser amounts than those indicated above can be utilized.

In addition to a single phosphate ester, surfactant compositions of the present invention may be prepared from mixtures of two or more of the phosphate esters described above.

(b) Polyoxyalkylene alkyl amine

The second essential component of the surfactant compositions of the present invention is a polyoxyalkylene alkyl amine. As is well known to those skilled in the art, these materials are amphoteric being nonionic under neutral or basic conditions are cationic under acidic conditions. These materials are prepared by reacting an alkylene oxide or a mixture of alkylene oxides, preferably ethylene and/or propylene oxide, with an alkyl amine. These amines are preferably primary amines in which the nitrogen atom is attached to a terminal carbon atom of the alkyl group. The amines are generally derived from naturally occurring products such as tallow, coconut, soybean, or cotton seed oils and as such, they are a mixture of amines in which the alkyl groups contain from 12 to 18 carbon atoms. Synthetic alkyl amines in which the alkyl groups contain from 12 to 18 carbon atoms may also be utilized. The polyoxyalkylene derivatives are prepared by reacting the alkylene oxide with the alkyl amine at elevated temperature and pressure in either one or two steps. Procedures for carrying out these reactions are well known to those skilled in the art.

The total amount of alkylene oxide used in the preparation of these materials is generally equal to from about 1 to about 20 mols per mol of amine. When 2 mols are used the resulting product is the N,N-bis(2-hydroxyalkyl)alkyl primary amine. When greater than 2 mols of alkylene oxide are used it is preferred to prepare the polyoxyalkylene alkyl amine in two steps. In the first step the alkyl amine is reacted with 2 mols of alkylene oxide to prepare an N,N-bis(2-hydroxyalkyl)alkyl amine which is then reacted with additional alkylene oxide in the presence of a basic catalyst to prepare the desired product. Preferred results are achieved with alkyl amine derivatives prepared with from about 2 to about 10 mols of alkylene oxide per mol of amine. Especially satisfactory results have been achieved with either (a) a material prepared from 5 mols of ethylene oxide and identified as polyoxyethylene(3)N,N-bis(2-hydroxyethyl)alkyl amine in which the alkyl amine is derived from tallow (often referred to as primary tallow amine) or (b) N,N-bis-(2-hydroxyethyl)tallow amine is utilized in the surfactant composition.

As in the case of the phosphate ester, the amount of amine derivative utilized can be varied over a wide range depending upon the same factors as discussed above in connection with the phosphate esters. Generally, satisfactory results in a variety of media and with a variety of pesticides have been achieved with from about 14 to about 50% by weight of this component based on the total weight of the surfactant composition. Particularly useful compositions have been prepared containing from about 20 to about 30% by weight of this component. It is believed that this material increases the soft water performance of emulsions or suspensions prepared from concentrated formulations containing these compositions. With less than about 14% by weight of this material the soft water performance begins to drop off. Also, when greater than about 50% by weight is used, performance in liquid fertilizer and very hard water is adversely affected.

As with the phosphate ester, surfactant compositions of the present invention may be prepared from mixtures of two or more of these polyoxyalkylene alkyl amines.

(c) Third Component

The final essential component of the surfactant compositions of the present invention is selected from the group consisting of nonionic polyoxyalkylated surfactants, polyhydric alcohol esters and polyoxyalkylene glycols. Of these, it is preferred to employ a nonionic polyoxyalkylated surfactant as the third component. When such a surfactant is employed it is essential that the surfactant be polyoxyalkylated and nonionic. The amphoteric alkyl amine surfactants described above may not be utilized as this component. Suitable nonionic polyoxyalkylated surfactants which may be utilized include, for example, polyoxyethylene(70)nonyl phenol; polyoxyethylene(10)nonyl phenol; polyoxyethylene(10)cetyl alcohol; polyoxyethylene(6)tridecyl alcohol; polyoxyethylene(20)sorbitan mono tall oil; alpha-alkyl polyoxyethylene polyoxypropylene block copolymers; polyoxyethylene(4)lauryl alcohol; polyoxyethylene(40)stearic acid; polyoxyethylene(4)sorbitan monolaurate; formaldehyde condensates of alkoxylated alkyl phenols; and polyoxyethylene(20) sorbitan monolaurate. An especially preferrred polyoxyalkylated nonionic surfactant for use as this component in the surfactant compositions of the present invention is prepared by reacting ethylene oxide with castor oil. As is well known in the art, castor oil is a triglyceride of the unsaturated hydroxy acid, ricinoleic acid. These materials are prepared by combining ethylene oxide with castor oil and heating the mixture under pressure in an autoclave for a suitable period of time—i.e., until essentially all of the ethylene oxide has reacted. The amount of ethylene oxide used is generally equal to from about 5 mols to about 55 mols per mol of castor oil. An especially useful emulsifier composition has been prepared utilizing a polyoxyalkylated nonionic surfactant prepared from 40 mols of ethylene oxide and identified as polyoxyethylene(40)castor oil. Another especially preferred material for use as this component in the surfactant compositions of the present invention is a polyoxyethylene polyoxypropylene block copolymer of butanol having an average molecular weight of from about 2000 to about 5000 and preferably from about 2400 to about 4000.

In addition to the preferred nonionic surfactants, either (a) a polyhydric alcohol ester such as sorbitan monolaurate, sorbitan monooleate, sorbitan monopalmitate, sorbitan monostearate or a monoglyceride of a fatty acid or (b) a polyoxyalkylene glycol such as a polyoxyethylene glycol or a polyoxypropylene glycol or a mixed polyoxyethylene polyoxypropylene glycol may be utilized as this component.

As in the case of the other two components, the amount of the third component utilized in the surfactant compositions of the present invention is not narrowly critical. However, particularly satisfactory results have been achieved with amounts equal to from about 5 to about 50% by weight of this component based upon the total weight of the surfactant composition. Especially preferred surfactant compositions have been prepared containing 10 and 30% by weight of this component. This material appears to enhance the performance of the surfactant compositions of the present invention both in a variety of naturally occurring waters as well as in liquid fertilizers and to lessen the sensitivity of the required ratio of the other two components.

Most of the individual components discussed above are liquids at room temperature. However, in the case of those containing a large polyoxyalkylene chain, some of the materials may be waxy at room temperature and if this is the case, the materials can be heated prior to mixing. The surfactant compositions of the present invention are prepared by simply blending the three components together. Any suitable equipment, such as a conventional mixer, may be used. The order of combining the materials is not important and they may be combined in any order. As mentioned above, the amounts of the individual components utilized can be varied somewhat depending upon a variety of factors and, particularly, the ultimate application of the composition. However, a general purpose emulsifier composition useful with a variety of pesticides and in waters of a wide range of hardness and liquid fertilizers contains 67% by weight of polyoxyethylene(8)nonyl phenol phosphate ester, 23% by weight of polyoxyethylene(3)-N,N-bis(2-hydroxyethyl)alkyl amine wherein the alkyl groups contain a mixture of from 14 to 18 carbon atoms and the amine is derived from soybean oil, and 10% by weight of polyoxyethylene(40)castor oil. Another emulsifier composition which has been found to be particularly useful contains 42% by weight of polyoxyethylene(8-)nonyl phenol phosphate ester, 28% by weight of N,N-bis(2-hydroxyethyl)alkyl amine wherein the alkyl groups contain a mixture of from 14 to 18 carbon atoms and the amine is derived from tallow, and 30% by weight of a polyoxyethylene polyoxypropylene block copolymer of butanol which has a average molecular weight of from 2400 to 3500.

In addition to the three essential components described above, the surfactant compositions of the present invention may contain one or more additional components including an anionic surfactant such as calcium dodecyl benzene sulfonate.

PESTICIDE FORMULATIONS

As noted above, the surfactant compositions of the present invention are particularly useful in the preparation of pesticide-containing emulsifiable concentrates. These concentrates generally contain a pesticide, a solvent for said pesticide and an emulsifier.

The emulsifiable concentrates of the present invention may be prepared with any pesticide generally utilized in the form of an emulsifiable concentrate. The emulsifiable concentrates of the present invention are not limited to a particular pesticide or a mixture of pesticides or to a particular organic solvent or mixture of organic solvents used to dissolve the pesticide. The pesticides and the organic solvents therefor are well known to those skilled in the art. Suitable pesticides which may be utilized include, for example, the following:

| TRADEMARK | COMMON NAME | CHEMICAL NAME |
| --- | --- | --- |
| PROWL | penoxalin | N-(1-ethylpropyl)-2,6-dinitro-3,4-xylidene |
| TREFLAN | trifluralin | 2,6-dinitro-N,N-dipropyl-4-trifluoromethylaniline |
| DURSBAN | chlorpyrifos | O,O-diethyl-O-(3,5,6-trichloro-2-pyridyl)-phosphorothioate |
| TOLBAN | profluralin | N-(cyclopropylmethyl)-2,6-dinitro-N-propyl-4-trifluoromethylanilene |
| COBEX | dinitramine | N'N'-diethyl-2,6-dinitro-4-trifluoromethyl-m-phenylenediamine |
| LASSO | alachlor | 2-chloro-2',6'-diethyl-N-(methoxymethyl)acetanilide |
| CHLORO-IPC | chlorpropham | isopropyl-N-(3-chlorophenyl) carbamate |
| FOLEX | merphos | tributyl phosphorotrithioite |
| DUAL | metolachlor | alpha-chloro-2'-ethyl-6'-methyl-N-(1-methyl-2-methoxyethyl)acetanilide |
| SUTAN | butylate | S-ethyl di-isobutylthiocarbamate |
| BASALIN | fluchloralin | N-(2-chloroethyl)-alpha-alpha-alpha-trifluoro-2,6-dinitro-N-propyl-p-toluidine |
| N-SERVE | nitrapyrin | 2-chloro-6-trichloromethylpyridine |
| EPTAM | EPTC | S-ethyl dipropylthiocarbamate |
| VERNAM | vernolate | S-propyl dipropylthiocarbamate |
| MOCAP | ethoprop | O-ethyl S,S-dipropyl phosphorodithioate |
| DYFONATE | fonofos | O-ethyl-S-phenyl ethylphosphonodithioate |

Emulsifiable concentrates may be prepared from these pesticides utilizing the surfactant compositions of the present invention. These concentrates generally contain 1–8 pounds of active ingredient per gallon. The amounts selected are those at which these pesticides are generally available. Preferred results are achieved with emulsifiable concentrates prepared with the following pesticides, all of which are identified by common name as in the above list; penoxalin, alachlor, metolachlor, butylate and nitrapyrin.

Preferred results have been achieved with emulsifiable concentrates containing herbicides and specifically alpha-haloacetanilides some of which are described in U.S. Pat. No. 3,442,945. Of the alpha-haloacetanilides especially preferred results have been achieved with the pesticide identified by the common name alachlor and identified chemically as 2-chloro-2',6'-diethyl-N-(methoxymethyl)acetanilide and with the pesticide identified by the common name metolachlor and identified chemically as alpha-chloro-2'-ethyl-6'-methyl-N-(1-methyl-2-methoxyethyl) acetanilide.

The organic solvents used in these concentrates may be any of those which are conventionally employed in the preparation of said concentrates. Generally, these solvents are those which will dissolve the pesticide utilized and are compatible with said pesticide. Typical examples of organic solvents which have been utilized include toluene, xylene, ethylbenzene, chlorobenzene, monomethyl naphthalenes, dimethyl naphthalenes, trimethyl naphthalenes, methyl naphthalenes, kerosene, and pine oil. A number of these aromatic solvents are commercially available under the following commercial designations: VELSICOL AR-50 (Vesicol Corp., Chicago, Il.); SUN 1547 (Sun Oil Co.); SHELL E-47 (Shell Oil Co.); SOLVESSO 100 (Standard Oil Co. of New Jersey); TENNECO 500-100 and TENNECO 400 (Tenneco Chemicals Inc.).

The relative amounts of pesticide, organic solvent and emulsifier in the emulsifiable concentrates of this invention are not narrowly critical and can vary over a wide range. However, it has generally been found that satisfactory emulsifiable concentrates useful in a variety of aqueous media are obtained containing from about 10% to about 70% by weight of pesticide, from about 2% to about 10% by weight of the emulsifier composition, and from about 28% to about 88% by weight of the organic solvent.

Pesticide emulsions for use in agriculture and related applications can be prepared from the emulsifiable concentrates of the present invention by simply adding the concentrate to a suitable aqueous medium. As indicated above, these concentrates will form stable emulsions in virtually any naturally occurring water ranging from very soft water—i.e., that containing 0 ppm calcium carbonate equivalent, to very hard water containing up to about 1,000 to 2,000 ppm calcium carbonate equivalent. Also, the emulsifiable concentrates will form stable emulsions when added to a liquid fertilizer composition. The emulsions can be prepared in any conventionally used equipment such as airplane spray tanks, napsack spray tanks, cattle dipping vats, farm equipment utilized in ground spraying, and the like.

Generally, the amount of emulsifiable concentrate used is equal to from about 0.1% to about 50% by volume based upon the total volume of the emulsion.

The surfactant compositions described above are also useful in the preparation of other concentrated pesticide-containing formulations such as wettable powders and flowables. As in the case of emulsifiable concentrates any pesticide conventionally used in one of these types of formulations may be utilized. In the case of a wettable powder, the pesticide, if solid, is finely ground and combined with a suitable solid diluent and the surfactant composition of the present invention. If a liquid pesticide is utilized, it is combined with a suitable adsorbent carrier and the surfactant composition. In the case of a flowable the pesticide and surfactant composition are combined with a minimal amount of water—i.e., just enough to prepare a stable dispersion. Both the wettable powders and flowable formulations of the present invention, form stable suspensions in waters of varying hardnesses and in liquid fertilizers.

In order to describe the present invention so that it may be more clearly understood, the following examples are set forth.

The following solvents and materials were used in the examples:

TERGITOL XD refers to a polyoxyethylene polyoxypropylene block copolymer of butanol having a specific gravity (40°/20° C.) of 1.053 and, as a 1% aqueous solution, a cloud point of 75° C. This material is commercially available from Union Carbide Corporation.

Aromatic solvent A refers to an aromatic petroleum distillate having a total aromatics content of 98.2% by volune, a mixed aniline point of 13.5° C., a Kauri-butanol value of 92, a flash point (TCC) of 110° F., a specific gravity at 60° F. of 0.874 and a distillation range from an initial boiling point of 312° F. to a dry point of 342° F.

Aromatic solvent B refers to an aromatic petroleum distillate having a total aromatics content of 95% by volume, a Kauri-butanol value of 90, a flash point (TCC) of 108° F., a specific gravity at 60° F. of 0.871 and a distillation range from an initial boiling point of 314° F. to a dry point of 409° F.

Preparations A–C illustrate the preparation of individual components of surfactant compositions of the present invention.

PREPARATION A

Preparation of Polyoxyethylene(8)Nonyl Phenol Phosphate Ester 1 mol of nonyl phenol was reacted with 8 mols of ethylene oxide by heating under pressure with a basic catalyst in an autoclave until essentially all of the ethylene oxide had reacted. The resulting product was identified as polyoxyethylene(8)nonyl phenol.

Into a reaction vessel containing 3 mols of polyoxyethylene(8)nonyl phenol there was added gradually over a period of time 1 mol of phosphoric anhydride ($P_2O_5$). The reaction was exothermic and external cooling was provided to control the temperature. After all of the $P_2O_5$ had been added the reaction mixture was stirred until essentially all of the $P_2O_5$ had reacted. The resulting product was identified as polyoxyethylene(8)nonyl phenol phosphate ester and was a mixture of the mono- and di-esters.

PREPARATION B

Preparation of Polyoxyethylene(3)N,N-bis(2-hydroxyethyl)alkyl amine 1 mol of N,N-bis(2-hydroxyethyl)primary soya amine (soya amine is a primary alkyl amine containing a mixture of alkyl groups each of which contains from 14 to 18 carbon atoms) was combined with 3 mols of ethylene oxide and heated under pressure and in the presence of a basic catalyst in an autoclave until essentially all of the ethylene oxide had reacted. The resulting product was identified as polyoxyethylene(3)-N,N-bis-(2-hydroxyethyl)$C_{14}$–$C_{18}$alkyl amine.

PREPARATION C

Preparation of Polyoxyethylene(40)Castor Oil 1 mol of castor oil (ricinoleic acid triglyceride) was reacted with 40 mols of ethylene oxide by heating in the presence of a basic catalyst under pressure in an autoclave until essentially all of the ethylene oxide had reacted. The resulting product was identified as polyoxyethylene(40)castor oil.

Examples 1–15 illustrate the preparation of emulsifier compositions of the present invention. All percentages refer to percent by weight based upon the total weight of the composition.

EXAMPLE 1

A surfactant composition was prepared by mixing at room temperature in a suitable vessel, the following materials in the indicated percentages.

polyoxyethylene(8)nonyl phenol phosphate ester prepared as described in Preparation A—67%;

polyoxyethylene(3)N,N-bis(2-hydroxyethyl)alkyl amine prepared as described in Preparation B—23%;

polyoxyethylene(40)castor oil prepared as described in Preparation C—10%.

EXAMPLES 2-15

Utilizing the procedure described in Example 1, several additional surfactant compositions were prepared from the components and amounts listed in the following table. In all of these examples, "Component A" refers to polyoxyethylene(8)nonyl phenol phosphate ester; "Component B" refers to polyoxyethylene(3)N,N-bis(2-hydroxyethyl)$C_{14}$-$C_{18}$alkyl amine; and "Component C" refers to polyoxyethylene(40)castor oil. All amounts refer to percent by weight.

| Component | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| A | 65 | 68 | 71 | 75 | 78 | 62 | 65 | 70 | 72 | 55 | 59 | 63 | 67 | 71 |
| B | 30 | 27 | 24 | 20 | 17 | 28 | 25 | 20 | 18 | 30 | 26 | 22 | 18 | 14 |
| C | 5 | 5 | 5 | 5 | 5 | 10 | 10 | 10 | 10 | 15 | 15 | 15 | 15 | 15 |

Examples 16 to 30 illustrate the preparation of emulsifiable concentrates of the present invention. All of these were prepared by dissolving the pesticide in the organic solvent or solvents and adding the surfactant composition to the resulting solution. All percentages in these Examples are expressed as percent by weight based upon the total weight of the concentrate. For convenience all of the pesticides used in these examples are identified by their common name. The chemical composition of these materials was identified above and is not repeated here.

EXAMPLE 16

Alachlor technical containing 91% by weight active material—49.55%;

Mono-chlorobenzene—27.27%;

Aromatic solvent B—18.18%;

Emulsifier composition of Example 1—5.0%.

EXAMPLES 17-30

A standard solution was prepared containing:

Alachlor technical containing 91% by weight active material—49.55%;

mono-chlorobenzene—27.27%;

Aromatic Solvent B—18.18%; Emulsifier—5%.

Each of the surfactant compositions described in Examples 2 through 15 above were evaluated in this standard solution. All of these combinations resulted in a satisfactory emulsifiable concentrate. The surfactant compositions utilized are listed in the following table.

| Example | Emulsifier Composition (Number refers to Examples above) |
|---|---|
| 17 | 2 |
| 18 | 3 |
| 19 | 4 |
| 20 | 5 |
| 21 | 6 |
| 22 | 7 |
| 23 | 8 |
| 24 | 9 |
| 25 | 10 |
| 26 | 11 |
| 27 | 12 |
| 28 | 13 |
| 29 | 14 |
| 30 | 15 |

Examples 31 to 46 illustrate the preparation and evaluation of aqueous based emulsions prepared from emulsifiable concentrates of the present invention. The stability of these emulsions was evaluated utilizing the following equipment, waters, liquid fertilizers and procedure.

TUBES

The tubes used in the stability tests were 100 ml graduated cylinders having an overall height (without stopper) of 12 inches, no feet and a square bottom. The cylinders were fitted at the top with a #19 Standard Taper ground glass joint and were designed with 50±2.5 mm of space from the 100 ml mark to the top shoulder of the cylinder. The cylinder was calibrated so that the 0 to 5 ml marks together with the 90 ml mark, the 95 ml mark and 100 ml mark were accurate.

WATERS

Stability was evaluated in waters having varying degrees of hardness. The waters employed and their preparation are described below. In all of these samples, water hardness is calculated as parts per million (ppm) calcium carbonate ($CaCO_3$).

342 PPM WATER

A solution (Solution A) was prepared by dissolving 138.8 grams of magnesium chloride hexahydrate ($MgCl_2.6H_2O$) in 1405 ml of distilled water. A second solution (Solution B) was prepared by dissolving 303.7 grams of anhydrous calcium chloride ($CaCl_2$) in 1405 ml of distilled water. The desired water was prepared by diluting 30 ml of Solution A and 30 ml of Solution B to 20 liters with distilled water.

114 WATER

This water was prepared by combining 1 part of 342 ppm water prepared as described above with 2 parts of distilled water.

1000 PPM WATER

This water was prepared by dissolving 2.9382 grams of calcium chloride dihydrate ($CaCl_2.2H_2O$) in 2 liters of distilled water.

LIQUID FERTILIZERS

Stability was evaluated in several liquid fertilizers. The fertilizers used and their preparation are described below.

Uran 28

A solution was prepared from the following materials:

ammonium nitrate—38.79%;
urea—31.00%;
distilled water—30.21%.

Uran 32

A solution was prepared from the following materials:
ammonium nitrate—44.24%;
urea—35.39%;
distilled water—20.37%.

4-10-10

A solution was prepared from the following materials:
3-18-18 liquid fertilizer available from NACHURS PLANT FOOD CO.—56.0%;
Uran 28 as described above—8.0%;
distilled water—36.0%.

PROCEDURE

To a standard tube as described above there was added 95 ml of a test liquid (either water or liquid fertilizer). To the test liquid there was then added 5 ml of the emulsifiable concentrate being evaluated. The tube was stoppered and inverted a specified number of times to mix the materials. It was then allowed to stand at ambient temperature and the separation, if any, was measured after stated periods of time. As noted above, the tubes are calibrated to indicate the percent separation achieved. The numerical results given for stability in these examples refer to volume percent separation as determined by a visual inspection of the tubes. The term "Stable" indicates that there was no visible separation. The term "Trace" refers to a separation of less than about ½% by volume—i.e., less than ½ ml of separation in the 100 ml standard tubes used. In evaluating stability, three criteria were used as follows:
Flocculation as indicated by the build-up of solid materials in the tube.
Cream as indicated by a dense creamy layer of separation in the tube.
Oil as indicated by the separation of an oily layer in the tube.
Of these, flocculation or oil within a relatively short period of time is undesirable. Although creaming is not desirable, a reasonable amount of creaming will not destroy the utility of the emulsion since cream is generally readily redispersible by agitation of the emulsion.

EXAMPLE 31

An emulsion was prepared by adding 5 ml of the emulsifiable concentrate described in Example 16 above to 95 ml of 114 ppm water contained in a 100 ml graduated cylinder as described above. The graduated cylinder was stoppered, inverted 15 times and allowed to stand at room temperature. The stability of the emulsion was evaluated periodically. After 1 hour the emulsion was still stable and there was no evidence of flocculation, creaming or oiling. After 24 hours there was a trace of cream present. The cylinder was reinverted 5 times and allowed to stand for 15 minutes. At the end of this time the emulsion was still stable with no flocculation, oiling or creaming.
The test was repeated with 342 ppm water and with 1000 ppm water and identical results were obtained.

EXAMPLES 32-40

Utilizing the procedure described in Example 21, several additional emulsifiable concentrates prepared as described in the examples above were evaluated in waters having a range of hardness. The emulsifiable concentrates (numbers refer to examples above) and waters used and the results obtained are given in the following table.

| EXAMPLE | EMULSIFIABLE CONCENTRATE | WATER (ppm) | RESULTS | | |
|---|---|---|---|---|---|
| | | | 1 HOUR | 24 HOURS | REINVERSION PLUS 15 MIN. |
| 32 | 18 | 114 | Stable | Stable | Stable |
| 33 | 18 | 342 | Stable | Trace Cream | Stable |
| 34 | 18 | 1,000 | Stable | 1% Cream | Trace Cream |
| 35 | 23 | 114 | Stable | Trace Cream | Stable |
| 36 | 23 | 342 | Stable | Trace Cream | Stable |
| 37 | 23 | 1,000 | Stable | Trace Cream | Stable |
| 38 | 28 | 114 | Stable | ½% Cream | Stable |
| 39 | 28 | 342 | Stable | ½% Cream | Stable |
| 40 | 28 | 1,000 | Stable | ½% Cream | Stable |

EXAMPLE 41

An emulsion was prepared by adding 5 ml of the emulsifiable concentrate described in Example 16 above to 95 ml of Uran 28 liquid fertilizer contained in a 100 ml graduated cylinder as described above. The graduated cylinder was stoppered, inverted 15 times and allowed to stand at room temperature. The stability of the emulsion was evaluated periodically. After 15 minutes the emulsion was still stable and there was no evidence of flocculation, creaming or oiling. After 30 minutes there was a trace of cream and after 45 minutes there was still only a trace of cream. After 1 hour there was ½% cream.

EXAMPLES 42-44

Utilizing the procedure described in Example 41, several additional emulsifiable concentrates prepared as described in the examples above were evaluated in URAN 28 liquid fertilizer. The emulsifiable concentrates used (numbers refer to examples above) and the results obtained are given in the following table.

| EXAMPLE | EMULSIFIABLE CONCENTRATE | RESULTS | | | |
|---|---|---|---|---|---|
| | | 15 MIN. | 30 MIN. | 45 MIN. | 1 HOUR |
| 42 | 18 | Stable | Trace Cream | ½% Cream | ½% Cream |
| 43 | 23 | Trace Cream | Trace Cream | ½% Cream | ½% Cream |
| 44 | 28 | Stable | Stable | Trace | ½% |

-continued

| EXAMPLE | EMULSIFIABLE CONCENTRATE | RESULTS | | | |
|---|---|---|---|---|---|
| | | 15 MIN. | 30 MIN. | 45 MIN. | 1 HOUR |
| | | | | Cream | Cream |

EXAMPLE 45

An emulsion was prepared by adding 5 ml of the emulsifiable concentrate described in Example 16 above to 95 ml of URAN 32 liquid fertilizer contained in a 100 ml graduated cylinder as described above. The graduated cylinder was stoppered, inverted 30 times and allowed to stand at room temperature. The stability of the emulsion was evaluated periodically. After 5 minutes the emulsion was still stable and there was no evidence of flocculation, creaming or oiling. After 15 minutes there was ½% of cream.

EXAMPLE 46

An emulsion was prepared by adding 5 ml of the emulsifiable concentrate described in Example 16 above to 95 ml of 4-10-10 liquid fertilizer contained in a 100 ml graduated cylinder as described above. The graduated cylinder was stoppered, inverted 30 times and allowed to stand at room temperature. The stability of the emulsion was evaluated periodically. After 5 minutes there was ½% of cream and after 15 minutes 5% of cream.

Examples 47-55 show the compatibility of the emulsifiable concentrates of the present invention with commercially available pesticide compositions. The commercially available pesticides used are identified as follows:

AATREX 4L, a flowable formulation containing 4 pounds per gallon active ingredient. The principal active ingredient is identified by the common name atrazine and chemically as 2-chloro- 4-ethylamino-6-isopropylamino-1,3,5-triazine.

AATREX 80W, a wettable powder containing 80 percent by weight atrazine.

BLADEX 50W, a wettable powder containing 50 percent by weight active ingredient. The active ingredient is identified by the common name cyanazine and chemically as 2-chloro-4-(1-cyano-1-methylethylamino)-6-ethylamino-1,3,5-triazine.

LOROX 50W, a wettable powder containing 50 percent by weight active ingredient. The active ingredient is identified by the common name linuron and chemically as 3-(3,4-dichlorophenyl)-1-methoxy-1-methylurea.

BANVEL 4S, a water solution containing 4 pounds per gallon of active ingredient. The active ingredient is identified by the common name dicamba and chemically as 3,6-dichloro-2-methoxybenzoic acid.

ALANAP PLUS, an emulsifiable concentrate containing 2 pounds per gallon of ALANAP identified by the common name naptalam and chemically as N-1-naphthylphthalamic acid, sodium salt and 1⅓ pounds per gallon of CHLORO-IPC identified by the common name chlorpropham and chemically as isopropyl-N-(3-chlorophenyl)carbamate.

DOW GENERAL Weed Killer, an emulsifiable concentrate containing 5 pounds per gallon of active ingredient identified by the common name dinoseb and chemically as 2-sec-butyl-4,6-dinitrophenol.

EXAMPLE 47

A suspension was prepared by adding 3 grams of AATREX 4L to 95 ml of 342 ppm water contained in a 100 ml graduated cylinder as described above. The graduated cylinder was stoppered and inverted 10 times. There was then added 5 ml of the emulsifiable concentrate described in Example 16 above. The graduated cylinder was stoppered, inverted 30 times and allowed to stand at room temperature. The stability of the emulsion was evaluated periodically. After 5 minutes the emulsion was still stable and there was no evidence of flocculation, creaming or oiling. After 15 minutes and again after 30 minutes there was ½% cream.

EXAMPLES 48-53

Utilizing the procedure described in Example 47, the compatibility of the emulsifiable concentrate described in Example 16 with several additional commercial pesticide formulations was evaluated. The commercial pesticides and amounts of each used and the results obtained are given in the following table.

| EXAMPLE | COMMERCIAL PESTICIDE | | RESULTS (All numbers refer to vol. % Cream) | | |
|---|---|---|---|---|---|
| | TYPE | AMOUNT | 5 MIN. | 15 MIN. | 30 MIN. |
| 48 | AATREX 80WP | 2 gms | Trace Cream | ½ | ½ |
| 49 | BLADEX 50WP | 2.5 gms | 8 | 6 | 6 |
| 50 | LOROX 50WP | 2.5 gms | 4 | 4 | 4½ |
| 51 | BANVEL 4S | 1 ml | Stable | 1 | 1 |
| 52 | ALANAP PLUS | 10 ml | Trace Cream | 2 | 4½ |
| 53 | DOW GENERAL Weed Killer | 10 ml | 1 | 6 | 9 |

EXAMPLES 54-55

The procedure of Example 47 was repeated except that 95 ml of URAN 28 liquid fertilizer was used instead of the 342 ppm water. The commercial pesticides and amounts of each used and the results obtained are given in the following table.

| EXAMPLE | COMMERCIAL PESTICIDE TYPE | AMOUNT | RESULTS 5 MIN. | 15 MIN. | 30 MIN. |
|---|---|---|---|---|---|
| | | | (All numbers refer to vol. % Cream) | | |
| 54 | AATREX 4L | 3 gms | Stable | Stable | ½ |
| 55 | DOW GENERAL Weed Killer | 10 ml | Trace Cream | 1 | 1 |

Examples 56–60 illustrate the preparation of flowable formulations of the present invention. All of these were prepared by combining the materials listed in the examples with 1000 grams of cylindrical balls and rolling for 16 hours on a ball mill. The milling procedure reduced the particle size to about 1–10 microns.

EXAMPLE 56

Carbaryl technical (1-naphtyl methylcarbamate)—133.2 gms.
Citric acid—0.75 gms;
1% KELZAN xanthane gel base (thickener)—30 gms;
ethylene glycol—12 gms;
342 ppm water—108.45 gms;
Dow Corning Silicone Antifoam FG-10 antifoam agent)—0.6 gms;
Surfactant composition of Example 1—15 gms.

EXAMPLE 57

Sulfur technical—168 gms;
1% KELZAN xanthane gel base—30 gms;
ethylene glycol—12 gms;
FG-10—0.6 gms;
342 ppm water—80.4 gms;
Surfactant composition of Example 1—9 gms.

EXAMPLE 58

Atrazine technical (2-chloro-4-ethylamino-6-isopropylamino-1,3,5-triazine)—141 gms;
1% KELZAN xanthane gel base—30 gms;
ethylene glycol—12 gms;
FG-10—0.6 gms;
342 ppm water—101.4 gms;
Surfactant composition of Example 1—15 gms.

EXAMPLE 59

Chlorothalonil technical (2,4,5,6-tetrachloro-1,3-dicyanobenzene)—170.7 gms;
1% KELZAN xanthane gel base—30 gms;
ethylene glycol—12 gms;
FG-10—0.6 gms;
342 ppm water—71.7 gms;
Surfactant composition of Example 1—15 gms.

EXAMPLE 60

Cyanazine technical (2-chloro-4-(1-cyano-1-methylethylamino)-6-ethylamino-1,3-5-triazine)—141 gms;
1% KELZAN xanthane gel base—30 gms;
ethylene glycol—12 gms;
FG-10—0.6 gms;
342 ppm water—101.4 gms;
Surfactant composition of Example 1—15 gms.

Examples 61–67 illustrate the preparation and evaluation of aqueous based suspensions prepared from flowable formulations of the present invention. The stability was evaluated as described above under Examples 31–46.

EXAMPLE 61

A suspension was prepared by adding 5 ml of the flowable formulation described in Example 56 above to 95 ml of 342 ppm water contained in a 100 ml graduated cylinder as described above. The graduated cylinder was stoppered, inverted 10 times and allowed to stand at room temperature. The stability of the suspension was evaluated periodically. After 15 minutes there was ½% cream which increased to 1% after 30 minutes and to 1½% after 1 hour.

EXAMPLES 62–67

Utilizing the procedure described in Example 61, the flowable formulations described above were evaluated in aqueous media. The formulations (numbers refer to examples above) and aqueous media utilized and the results obtained are given in the following table. All of the numbers in the results refer to volume percent cream.

| EXAMPLE | FLOWABLE FORMULATION | AQUEOUS MEDIUM | RESULTS 15 MINUTES | 30 MINUTES | 1 HOUR |
|---|---|---|---|---|---|
| 62 | 57 | 342 ppm water | Stable | Trace Cream | ½% |
| 63 | 58 | 342 ppm water | Trace Cream | Trace Cream | ½% |
| 64 | 59 | 342 ppm water | 2% | 2½% | 3% |
| 65 | 60 | 342 ppm water | Trace Cream | ½% | 1% |
| 66 | 58 | URAN 28 liq. fertilizer | Stable | Stable | Stable |
| 67 | 60 | URAN 28 liq. fertilizer | Stable | Slight Flocculation | Slight Flocculation |

Preparations D–F illustrate the preparation of individual components of surfactant compositions of the present invention.

PREPARATION D

Preparation of Polyoxyethylene(10)Nonyl Phenol Phosphate Ester 1 mol of nonyl phenol was reacted with 10 mols of ethylene oxide by heating under pressure with a basic catalyst in an autoclave until essentially all of the ethylene oxide had reacted. The resulting product was identified as polyoxyethylene(10)nonyl phenol.

Into a reaction vessel containing 3 mols of polyoxyethylene(10)nonyl phenol there was added gradually over a period of time 1 mol of phosphoric anhydride ($P_2O_5$). The reaction was exothermic and external cooling was provided to control the temperature. After all of the $P_2O_5$ had been added the reaction mixture was stirred until essentially all of the $P_2O_5$ had reacted. The resulting product was identified as polyoxyethylene(10)nonyl phenol phosphate ester and was primarily a mixture of the mono- and di-esters.

PREPARATION E

Preparation of N,N-bis(2-hydroxyethyl)alkyl amine 1 mol of tallow amine (tallow amine is a primary alkyl amine containing a mixture of alkyl groups each of which contains from 14 to 18 carbon atoms) was combined with 2 mols of ethylene oxide and heated under pressure in an autoclave until essentially all of the ethylene oxide had reacted. The resulting product was identified as N,N-bis(2-hydroxyethyl)-$C_{14}$-$C_{18}$alkyl amine.

PREPARATION F

Preparation of Polyoxyethylene(8)N,N-bis(2-hydroxyethyl)alkyl amine 1 mol of N,N-bis(2-hydroxyethyl)$C_{14}$-$C_{18}$ alkyl amine prepared as described in Preparation E was combined with 8 mols of ethylene oxide and heated under pressure and in the presence of a basic catalyst in an autoclave until essentially all of the ethylene oxide had reacted. The resulting product was identified as polyoxyethylene(8)-N,N-bis(2-hydroxyethyl)$C_{14}$-$C_{18}$alkyl amine.

Examples 68–70 illustrate the preparation of emulsifier compositions of the present invention. All percentages refer to percent by weight based upon the total weight of the composition.

EXAMPLE 68

A surfactant composition was prepared by mixing at elevated temperature in a suitable vessel, the following materials in the indicated percentages.

polyoxyethylene(8)nonyl phenol phosphate ester prepared as described in Preparation A—42%;
N,N-bis(2-hydroxyethyl)alkyl amine prepared as described in Preparation E—28%;
Tergitol XD as described above—30%.

EXAMPLE 69

A surfactant composition was prepared by mixing at elevated temperature in a suitable vessel, the following materials in the indicated percentages.

polyoxyethylene(8)nonyl phenol phosphate ester prepared as described in Preparation A—21%;
polyoxyethylene(8)N,N-bis(2-hydroxyethyl)alkyl amine prepared as described in Preparation F—24.5%;
N,N-bis(2-hydroxyethyl)alkyl amine prepared as described in Preparation E—24.5%;
Tergitol XD—30%.

EXAMPLE 70

A surfactant composition was prepared by mixing at elevated temperature in a suitable vessel, the following materials in the indicated percentages.

polyoxyethylene(8)nonyl phenol phosphate ester prepared as described in Preparation A—21%;
polyoxyethylene(10)nonyl phenol phosphate ester prepared as described in Preparation D—21%;
N,N-bis(2-hydroxyethyl)alkyl amine prepared as described in Preparation E—28%;
Tergitol XD—30%.

Examples 71 and 72 illustrate the preparation of emulsifiable concentrates of the present invention. Both of these were prepared by dissolving the pesticide in the organic solvent or solvents and adding the surfactant to the resulting solution. All percentages in these Examples are expressed as percent by weight based upon the total weight of the concentrate. For convenience all of the pesticides used in these example are identified by their common name. The chemical composition of these materials was identified above and is not repeated here.

EXAMPLE 71

Metolachlor technical containing about 90–95% by weight active material—91%;
Aromatic Solvent A—2.0%;
Emulsifier composition of Example 68–7.0%.

EXAMPLE 72

Metolachlor technical containing about 91–95% by weight active material—91%;
Aromatic Solvent A—2.0%;
Emulsifier composition of Example 70–7.0%;

Utilizing the procedures and materials described above in connection with Examples 31–46 aqueous based emulsions were prepared from the emulsifiable concentrates described in Examples 71 and 72.

EXAMPLE 73

An emulsion was prepared by adding 5 ml of the emulsifiable concentrate described in Example 71 above to 95 ml of 342 ppm water contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling. After 24 hours there was ½% of cream present. The cylinder was reinverted 5 times and allowed to stand for 1 hour. At the end of this time the emulsion was still stable with no flocculation, oiling or creaming.

EXAMPLE 74

An emulsion was prepared by adding 3 ml of the emulsifiable concentrate described in Example 71 above to 97 ml of Uran 28 liquid fertilizer contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling.

EXAMPLE 75

An emulsion was prepared by adding 5 ml of the emulsifiable concentrate described in Example 72 above to 342 ppm water contained in a 100 ml graduated cylinder. The graduated cylinder was stoppered, inverted 15 times and allowed to stand at room temperature. The stability of the emulsion was evaluated periodically. After 1 hour there was a trace of cream present.

EXAMPLE 76

An emulsion was prepared by adding 3 ml of the emulsifiable concentrate described in Example 72 above to 97 ml of Uran 28 liquid fertilizer contained in a 100 ml graduated cylinder. The graduated cylinder was stoppered, inverted 15 times and allowed to stand at room temperature. The stability of the emulsion was evaluated periodically. After 30 minutes there was ½% cream.

EXAMPLE 77

A suspension was prepared by adding 0.5 ml of AA-TREX 4L to 9.0 ml of Uran 28 liquid fertilizer contained in a test tube. The test tube was inverted 10 times and there was then added 0.5 ml of the emulsifiable concentrate described in Example 71 above. The test tube was inverted 10 times and allowed to stand at room temperature. The stability of the emulsion was evaluated periodically. After 2 hours the emulsion ws still stable and there was no evidence of flocculation, creaming or oiling.

EXAMPLE 78

A surfactant composition was prepared by mixing at elevated temperature in a suitable vessel, the following materials in the indicated percentages by weight.
polyoxyethylene(8)nonyl phenol phosphate ester prepared as described in Preparation A—67%;
polyoxyethylene(8)N,N-bis(2-hydroxyethyl)alkyl amine prepared as described in Preparation F—9%;
N,N-bis(2-hydroxyethyl)alkyl amine prepared as described in Preparation E—14%;
polyoxyethylene(40)castor oil prepared as described in Preparation C—10%.

EXAMPLE 79

Utilizing the procedure described above in connection with Examples 71 and 72, an emulsifiable concentrate was prepared containing:
Alachlor technical containing 91% by weight active materials—49.55%;
mono-chlorobenzene—27.27%;
Aromatic Solvent B—18.18%;
Surfactant composition of Example 78–5.0%.

EXAMPLE 80

An emulsion was prepared by adding 5 ml of the emulsifiable concentrate described in Example 79 above to 95 ml of 342 ppm water contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling. After 24 hours there was a trace of cream present. The cylinder was reinverted 5 times and allowed to stand for 1 hour. At the end of this time the emulsion was still stable with no flocculation, oiling or creaming.

EXAMPLE 81

An emulsion was prepared by adding 5 ml of the emulsifiable concentrate described in Example 79 above to 95 ml of Uran 28 liquid fertilizer contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling.

EXAMPLE 82

A surfactant composition was prepared by mixing at elevated temperature in a suitable vessel, the following materials in the indicated percentages by weight.
polyoxyethylene(8)nonyl phenol phosphate ester prepared as described in Preparation A—67%
polyoxyethylene(3)N,N-bis(2-hydroxyethyl)alkyl amine prepared as described in Preparation B—23%
polyoxyethylene glycol having an average molecular weight of 1500—10%.

EXAMPLE 83

Utilizing the procedure described above in connection with Examples 71 and 72, an emulsifiable concentrate was prepared containing:
Alachlor technical containing 91% by weight active materials—49.55%;
mono-chlorobenzene—27.27%;
Aromatic Solvent B—18.18%;
Surfactant composition of Example 82—5.0%.

EXAMPLE 84

An emulsion was prepared by adding 5 ml of the emulsifiable concentrate described in Example 83 above to 95 ml of 342 ppm water contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling. After 24 hours there was a trace of cream present. The cylinder was reinverted 5 times and allowed to stand for 1 hour. At the end of this time the emulsion was still stable with no flocculation, oiling or creaming.

EXAMPLE 85

An emulsion was prepared by adding 5 ml of the emulsifiable concentrate described in Example 83 above to 95 ml of Uran 28 liquid fertilizer contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling.

EXAMPLE 86

A surfactant composition was prepared by mixing at room temperature in a suitable vessel, the following materials in the indicated percentages by weight.
polyoxyethylene(8) nonyl phenol phosphate ester prepared as described in Preparation A—67%;
polyoxyethylene(3)N,N-bis(2-hydroxyethyl)alkyl amine prepared as described in Preparation B—23%;
sorbitan monooleate—10%.

EXAMPLE 87

Utilizing the procedure described above in connection with Examples 71 and 72, an emulsifiable concentrate was prepared containing:
Alachlor technical containing 91% by weight active materials—49.55%;
mono-chlorobenzene—27.27%;
Aromatic Solvent B—18.18%;
Surfactant composition of Example 86—5.0%.

EXAMPLE 88

An emulsion was prepared by adding 5 ml of the emulsifiable concentrate described in Example 87 above to 95 ml of 342 ppm water contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling. After 24 hours there was a trace of cream present. The cylinder was reinverted 5 times and allowed to stand for 1 hour. At the end of this time the emulsion was still stable with no flocculation, oiling or creaming.

EXAMPLE 89

An emulsion was prepared by adding 5 ml of the emulsifiable concentrate described in Example 87 above to 95 ml of Uran 28 liquid fertilizer contained in a 100 ml graduated cylinder. The graduated cylinder was stoppered, inverted 15 times and allowed to stand at room temperature. The stability of the emulsion was evaluated periodically. After 1 hour the emulsion was still stable and there was no evidence of flocculation, creaming or oiling.

What is claimed is:

1. A surfactant composition comprising
   (a) a polyoxyethylene nonyl phenol phosphate ester,
   (b) a polyoxyethylene N,N-bis(2-hydroxyethyl) alkyl amine, wherein the alkyl contains from 12 to 18 carbon atoms, and
   (c) a polyoxyethylene castor oil,
wherein the amount of the polyoxyethylene nonyl phenol phosphate ester component is equal to from about 60% to about 80% by weight based upon the total weight of the composition, the amount of the polyoxyethylene N,N-bis(2-hydroxyethyl)alkyl amine is equal to from about 14% to about 30% by weight based upon the total weight of the composition and the amount of the polyoxyethylene castor oil is equal to from about 5% to about 15% by weight based upon the total weight of the composition.

2. A surfactant composition, as claimed in claim 1, containing 67% by weight based upon the total weight of the composition of polyoxyethylene(8)nonyl phenol phosphate ester, 23% by weight based upon the total weight of the composition of polyoxyethylene(3)N,N-bis(2-hydroxyethyl)alkyl amine and 10% by weight based upon the total weight of the composition of polyoxyethylene(40)castor oil.

3. A surfactant composition comprising
   (a) a polyoxyethylene nonyl phenol phosphate ester,
   (b) N,N-bis(2-hydroxyethyl)alkyl amine wherein the alkyl portion contains from 12 to 18 carbon atoms, and
   (c) a polyoxyethylene polyoxypropylene block copolymer of butanol,
wherein the amount of the polyoxyethylene nonyl phenol phosphate ester is equal to from about 20% to about 80% by weight based upon the total weight of the composition, the amount of the N,N-bis(2-hydroxyethyl)alkyl amine is equal to from about 14% to about 50% by weight based upon the total weight of the composition and the amount of copolymer of butanol is equal to from about 5% to about 50% by weight based upon the total weight of the composition.

4. A surfactant composition, as claimed in claim 3, containing 42% by weight based upon the total weight of the composition of polyoxyethylene(8)nonyl phenol phosphate ester, 28% by weight based upon the total weight of the composition of N,N-bis(2-hydroxyethyl)$C_{14}$–$C_{18}$ alkyl amine and 30% by weight based upon the total weight of the composition of a polyoxyethylene polyoxypropylene block copolymer of butanol having an average molecular weight of from 2,400 to 3,500.

* * * * *